(12) United States Patent
Ernst

(10) Patent No.: US 8,637,256 B2
(45) Date of Patent: Jan. 28, 2014

(54) IMMUNOASSAY FOR DETERMINING THE RELEASE OF NEUROTENSIN INTO THE CIRCULATION

(75) Inventor: Andrea Ernst, Hennigsdorf (DE)

(73) Assignee: Sphingotec GmbH, Borgsdorf (DE)

( * ) Notice: Subject to any disclaimer, the term of this patent is extended or adjusted under 35 U.S.C. 154(b) by 831 days.

(21) Appl. No.: 11/814,850

(22) PCT Filed: Jan. 25, 2006

(86) PCT No.: PCT/EP2006/000659
§ 371 (c)(1),
(2), (4) Date: Jul. 26, 2007

(87) PCT Pub. No.: WO2006/079528
PCT Pub. Date: Aug. 3, 2006

(65) Prior Publication Data
US 2008/0280306 A1 Nov. 13, 2008

(30) Foreign Application Priority Data
Jan. 26, 2005 (DE) .......................... 10 2005 003 687

(51) Int. Cl.
*G01N 33/53* (2006.01)
(52) U.S. Cl.
CPC ..................................... *G01N 33/53* (2013.01)
USPC .......... 435/7.1; 435/7.92; 435/7.94; 436/501; 436/172

(58) Field of Classification Search
None
See application file for complete search history.

(56) References Cited

U.S. PATENT DOCUMENTS

| | | | |
|---|---|---|---|
| 6,020,212 A | 2/2000 | Mathis | |
| 6,274,720 B1 * | 8/2001 | Lal et al. | ..................... 536/23.51 |
| 6,756,483 B1 | 6/2004 | Bergmann | |
| 6,849,714 B1 | 2/2005 | Bridon et al. | |
| 6,887,470 B1 | 5/2005 | Bridon et al. | |
| 7,498,139 B2 | 3/2009 | Bergmann | |
| 7,723,492 B2 | 5/2010 | Bergmann | |
| 7,972,799 B2 | 7/2011 | Bergmann | |
| 7,998,686 B2 | 8/2011 | Bergmann | |
| 2003/0109420 A1 | 6/2003 | Valkirs et al. | |
| 2007/0082363 A1 | 4/2007 | Bougueleret et al. | |

FOREIGN PATENT DOCUMENTS

| | | |
|---|---|---|
| EP | 0 622 458 | 11/1994 |
| EP | 0 656 121 | 3/1998 |
| JP | 07-196693 | 8/1995 |
| JP | 11-508357 | 7/1999 |
| JP | 2002-527753 | 8/2002 |
| WO | WO 00/22439 | 4/2000 |
| WO | WO 00/69900 | 11/2000 |
| WO | WO 02/08723 | 1/2002 |

OTHER PUBLICATIONS

Viken et al., Influence on Antibody Recognition of Amino Acid Substitutions in the Cleft of HLA-DQ2 molecules, Human Immunology 44, 1995, pp. 63-69.*
Allen et al., "Adult cystic fibrosis: postprandial response of gut regulatory peptides", Gastroenterology (Dec. 1983), 85, 1379-1383.
Bardella et al., "Gastric emptying and plasma neurotensin levels in untreated celiac patients", (2000) Scandinavian Journal of Gastroenterology 35: 269-73.
Barelli et al., "Role of endopeptidase 3.4.24.16 in the catabolism of neurotensin, in vivo, in the vascularly perfused dog ileum", (1994) British Journal of Pharmacology 112: 127+132.
Beck B., (2000), "Neuropeptides and obesity", Nutrition 16: 916-923.
Beinfeld M.C. (1998), "Prohormone and proneuropeptide processing, Recent progress and future challenges", Endocrine 8: 1-5.
Bissette et al., "Hypothermia and intolerance to cold induced by intracisternal administration of the hypothalamic peptide neurotensin", 1976 Nature 262: 607-9.
Carraway et al., "Posttranslational processing of the neurotensin/neuromedin-N precursor", (1992) Annals of the New York Academy of Sciences, 668:1-16.
Clineschmidt et al., "Antinocispnsive effects of neurotensin and neurotensin-related peptides", (1982), Annals of NY Academy Sciences 400:283-306.
Dobner et al., "Cloning and sequence analysis of cDNA for the canine neurotensin/neuromedin N precursor", (1987) PNAS USA 84:3516-3520.
Evers et al., (1992), "Neurotensin stimulates growth of colonic mucosa in young and aged rats", Gastroenterology 103: 86-91.
Ferraro et al., (1995), "Neurotensin increases endogenous glutamate release in the neostriatum of the awake rat", Synapse 20: 362-364.
Feurle et al., "Neurotensin induces hyperplasia of the pancreas and growth of the gastric antrum in rats", (1987) Gut 28 Suppl: 19-23.
Friry et al., "Production of recombinant large proneurotensinIneuromedin N-derived peptides and characterization of their binding and biological activity", (2002) Biochemical and Biophysical Research Communications 290: 1161-1168.
Gullo et al., "Plasma cholecystokinin and neurotensin after an ordinary meal in humans. A prolonged time study." (1998) Gastroenterological and Clinical Biology 22: 25-28.
Hammer et al., "Elevation of Plasma Neurotensinlike Immunoreactivity after a Meal", Journal of Clinical Investigation, vol. 70, Jul. 1982, 74-81.
Herzig et al., "Plasma Concentrations of Cholecystokinin and Neurotensin in Patients with Cystic Fibrosis", (1997) Scandinavian Journal of Gastroenterology 32; 315-319.
Kislauskis et al., "The Rat Gene Encoding Neurotensin and Neuromedin N. Structure, tissue-specific expression, and evolution of exon sequences", (1988) Journal of Biological Chemistry 263(10); 4963-4968.

(Continued)

*Primary Examiner* — Gary W Counts
(74) *Attorney, Agent, or Firm* — Millen, White, Zelano & Branigan, P.C.

(57) ABSTRACT

The invention relates to an immunodiagnostic method for determining the release of neurotensin into the circulation of mammals based on the selective determination of an immunoreactivity of the N-terminal portion of a mammal proneurotensin (PNT immunoreactivity) in a serum or plasma sample of a mammal; this immunoreactivity is not neurotensin or neuromedin immunoreactivity.

13 Claims, 5 Drawing Sheets

(56) References Cited

OTHER PUBLICATIONS

Kitabgi, Patrick, "Neurotensin Modulates Dopamine Neurotransmission at Several Levels along Brain Dopaminergic Pathways", (1989) Neurochemistry International 14(2): 111-119.
Lapchak et al., "Neurotensin regulation of endogenous acetylcholine release for rat cerebral cortex: effect of quinolinic acid lesions of the basal forebrain", (1990) Journal of Neurochemistry 55: 1397-1403.
Lee et al., "In vitro degradation of neurotensin in human plasma", (1986) Peptides 7: 383-387.
Murphy et al., "Gut Hormones and gastrointestinal motility in children with cystic fibrosis", (1992) Digestive Diseases and Sciences 37(2): 187-192.
Nustede et al., "Plasma concentrations of neurotensin and CCK in patients with chronic pancreatitis with and without enzyme substitution", (1991) Pancreas 6(3): 260-265.
Reinecke et al., "Localization of neurotensin immunoreactive nerve fibers in the guinea-pig heart: evidence derived by immunohistochemistry, radioimmunoassay and chromatography", (1982) Neuroscience 7(7): 1785-1795.
Rokaeus et al., "Occurrence, storage and release of neurotensin-like immunoreactivity from the adrenal gland", (1984) Acta Physiology Scandinavia 120: 373-80.
Rovere et al., "Pro-neurotensinlneuromedin n. expression and processing in human colon cancer cell lines", (1998), Biochemical and Biophysical Research Communications 246: 155-159.
Rokaeus et al., "Cigarette smoking potentiates fat-induced elevation of neurotensin-like immunoreactivity in human plasma", (1984) Acta Physiologica Scandinavia 121: 181-184.
Rosell et al., "The effect of ingestion of amino acids, glucose and fat on circulating neurotensin-like immunreactivity", (1979) Acta Physiologica Scandinavia 107: 263-267.
Rostene et al., "Interaction between neurotensin and dopamine in the brain. Morphofunctional and clinical evidence", (1992), Annals N Y Academy Sciences, 668:217-31.
Rowe et al., "Central administration of neurotensin stimulates hypothalamic-pituitary-adrenal activity. The paraventricular CRF neuron as a critical site of action", (1992), Annals N Y Academy Sciences 668: 365-7.
Schimpff et al., "Increased plasma neurotensin concentrations in patients with Parkinson's disease", (2001), Journal of Neurological and Neurosurgical Psychiatry 70: 784-786.
Schimpff et al., "Plasma neurotensin levels in humans: relation to hormone levels in diseases involving the hypothalamo-pituitary-thyroid axis", (1995), European Journal of Endocrinology 133: 534-538.
Stroud et al., "Signal sequence recognition and protein targeting", (1999), Current Opinion in Structural Biology 9: 754-9.
Vincent, J.P., "Neurotensin receptors: binding properties, transduction pathways, and structure", (1995), Cellular Molecular Neurobiology 15(5): 501-12.
Wilding, J.P., "Neuropeptides and appetite control", (2002), Diabetic medicine 19: 619-627.
Wisen et al., "Plasma concentrations of regulatory peptides in obesity following modified sham feeding (MSF) and a liquid test meal", (1992), Regulatory Peptides 39: 43-54.
Wood et al., "Neurotensin stimulates growth of small intestine in rats", (1988), American Journal of Physiology 255: G813-7.
Eklund et al., "Effects of cholera toxin, Escherichia coli heat stable toxin and sodium deoxycholate on neurotensin release from the ileum in vivo", Regulatory Peptides, vol. 26(3) (1989) 241-252.
Bidard et al., "Immunological and biochemical characterization of processing products from the neurotensin/neuromedin N precursor in the rat medullary thyroid carcinoma 6-23 cell line", Biochemal Journal (1993) 291(1), 225-233.
International Search Report for corresponding European patent application EP2006/000659, Aug. 2007.
Cyr, Melanie, et al., "Bradykinin and des-Arg$^9$-braclykinin metabolic pathways and kinetics of activation of human plasma," Am J Physiol Heart Circ Physicl 281:H275-H283, 2001.
Domschke, S., et al., "Vasoactive intestinal peptide in man pharmacokinetics, metabolic and circulatory effects[1]," Gut, 1978, 19, 1049-1053.
Eto, T., "A review of the biological properties and clinical implications of adrenomedullin and proadrenomedultin N-terminal 20 peptide (PAMP), hypotensive and vasodilating peptides," Peptides 22 (2001) 1693-1711.
Etoh, T., et al., "Differential Hormonal Profiles of Adrenomeduilin and Proadrenornedullin N-Terminal 20 Peptide in Patients with Heart Failure and Effect of Treatment on Their Plasma Levels," Clin. Cardiol. 22, 113-117 (1999).
Hunt, P.J., et al, "Bioactivity and Metabolism of C-Type Natriuretic Peptide in Normal Man", J of Clin Endocr and Metab, vol. 78, No. 6, 1428-1435, Jun. 1994.
Japp, A.G., et al., "Vascular Effects of Apelin in Vivo in Man," Journal of the American College of Cardiology (JACC), downloaded from content.onlinejacc.org on Apr. 5, 2011, JACC, vol. 52, No. 11, 2008, Sep. 9, 2008, 908-913.
Kimura, K., et al., "ANP is cleared mudh faster than BNP in patients with congestive heart failure," Eur J Clin Pharmacol (2007) 63:699-702.
Kitamura, K., et al., "Identification and hypotensive activity of proadrenomedullin N-terminal 20 peptide (PAMP)," FEBS Letters 351 (1994) 35-37.
Kraenzlin, M.E., et al., "Infusion of a novel peptide, calcitonin gene-related peptide (CGRP) in man. Pharmacokinetics and effects on gastric acid secretion and on gastrointestinal hormones," Regulatory Peptides, 10 1985 189-197.
Lewis, L.K., et al., "Adrenomedullin (1-52) measured in human plasma by radicimmunoassay: plasma concentration, adsorption, and storage," Clinical Chemistry 44;3, 571-577 (1998).
Lundberg, J.M., et al., "Evidence for Release of Endothelin-1 in Pigs and Humans," Journal of Cardiovascular Pharmacology, 17 (Suppl. 7):S350-S353, Dec. 1991.
Magness, R.R., Ph.D., et al., "Angiotensin II metabolic clearance rate and pressor responses in nonpregnant and pregnant women," Am J Obstet Gynecol, vol. 171, No. 3, 668-679, Sep. 1994.
Meeran, K., et al., "Circulating adrenomedullin does not regulate systemic blood pressure but increases plasma prolactin after intravenous infusion in humans: a pharmacokinetic study," J Clin Endocrinof Metab, 1997; 82:95-100.
Struck, J., et al., "Identification of an Adrenomedullin precursor fragment in plasma of sepsis patients," Peptides 25 (2004) 1369-1372.
Webster's New World Dictionary (of the American Language), Second College Edition, 1982, p. 1568.
Janeway et al., Immunology: the Immume System in Health and Disease Elsevier Science Ltd/Garland Publishing, NY, 4rh Edition, pp. 34-35, (1999).
Merck Manuals Online Medical Library, section index for "Heart and Blood Vessel Disorders"; Home Edition, retrieved from www.merck.com/mrnhe on Mar. 29, 2008, 2 pages.
Pio, R., et al., "Complement Factor H is a Serum-Binding Protein for Adrenomedullin, and the Resulting Complex Modulates the Bioactivities of Both Partners," J. of Biol. Chem., vol. 276, No. 15, Apr. 13, 2001, pp. 12292-12300.
Lewis, L.K., et al., "Adrenomedullin(1-62) measured in human plasma by radioimmunoassay, plasma concentration, adsorption, and storage," Clin. Chem., 44:3, 571.577 (1998).
Morgenthaler, N.G., et al., "Measurement of Midregional Proadrenomedullin in Plasma with an Immunoluminometric Assay," Clin. Chem., 51:10, 1623-1829 (2005).
"Adrenomedullin (AM(ADM) (45-92), Pro(Human) Product Spec Sheet; Phoenix Pharmaceuticals; Jan. 2010".
Harlow, E. and Lane, D., Antibodies: A Laboratory Manuarl (1998) Cold Spring Harbor Laboratory Press, Cold Spring Harbor, NY, pp. 53, 60-61, 72-76, 555, 559, 561 and 578-579.
Kennedy et al., "Expression of the Rat Adrenomedulin, Functional Response", Biochemical and Biophysical Research Communications, 244, pp. 832-837 (1998).
Richards et al. "Plasma N-Terminal Pro-Brain Natriuretic Peptide and Adrenomedullin", Circulation, (1998); 97, pp. 1921-1929.

(56) References Cited

OTHER PUBLICATIONS

Qi et al., "Effects of different peptide fragments derived from proadrenomedullin on gene expression of adrenomedullin gene", Peptides 23 (2002), pp. 1141-1147.

Kitamura K. et al., "Adrenomedullin and PAMP: Discovery, Structures, and Cardiovascular Functions," Microscopy Research and Technique; 57: pp. 3-13 (2002).

Ehlenz, K. et al., "High Levels of Circulating Adrenomedullin in Severe Illness: Correlation with C-Reactive Protein and Evidence Against the Adrenal Medulla as Site of Origin," Endocrinology & Diabetes, vol. 105, pp. 156-162 (1997).

Ueda, Shiro et al., Increased Plasma Levels of Adrenomedullin in Patients with Systemic Inflammatory Response Syndrome, AM.J. Respir. Care Med., vol. 160, pp. 132-136, (1999).

Struck, Joachim, et al., "Identification of an Adrenomedullin Precursor Fragment in Plasma of Sepsis Patients", Peptides, vol. 25, pp. 1369-1372, (2004).

Hrubec et al., "Plasma Versus Serum: Specific Differences in Biochemical Analyte Values", Journal of Avian Medicine and Surgery vol. 16(2), pp. 101-105, (2002).

Mathis et al., "Probing Molecular Interactions with Homogeneous Techniques Based on Rare Earth Cryptates and Fluorescence Energy Transfer", Clin. Chem. vol. 41(9), pp. 1391-1397 (1995).

Enomoto et al., "High Throughput Screening for Human Interferon-gamma Production Inhibitor Using Homogenous Time-resolved Fluorescence", J. Biomol. Screen, vol. 5,(4), pp. 263-268, Aug. 2000.

Kuby et al., Immunology, W.H. Freeman and Company, p. 125, (1992).

Bost et al., Immunol, Invest., vol. 17, pp. 577-586, (1968).

Bendayan, M.J. Histochern, Cytochern., vol. 43, pp. 881-886, (1995).

Wolfe, S.L., Molecular and Cellular Biology, pp. 790-793 (1993).

The Academic Press Dictionary of Science and Technology, Definition for the term "polyclonal"; Oxford: Elsevier Science & Technology (1996); retrieved Oct. 22, 2008 from http://www.credoreferonce.com/entry/344515/.

Tikhonov et al., Neph. Dial. Transplant. vol. 12 (12), pp. 2557-2561, (1997).

Office Action issued for Japanese Patent Application No. 2006-504400, dated Jun. 17, 2009 (with translation—8 pages), Jun. 17, 2009.

\* cited by examiner

SEQUENCE LISTING

<160> NUMBER OF SEQ ID NOS: 6

<210> SEQ ID NO 1
<211> LENGTH: 170
<212> TYPE: PRT
<213> ORGANISM: Homo Sapiens

<400> SEQUENCE: 1

Met Met Ala Gly Met Lys Ile Gln Leu Val Cys Met Leu Leu Leu Ala
1               5                   10                  15

Phe Ser Ser Trp Ser Leu Cys Ser Asp Ser Glu Glu Met Lys Ala
            20                  25                  30

Leu Glu Ala Asp Phe Leu Thr Asn Met His Thr Ser Lys Ile Ser Lys
        35                  40                  45

Ala His Val Pro Ser Trp Lys Met Thr Leu Leu Asn Val Cys Ser Leu
    50                  55                  60

Val Asn Asn Leu Asn Ser Pro Ala Glu Glu Thr Gly Glu Val His Glu
65                  70                  75                  80

Glu Glu Leu Val Ala Arg Arg Lys Leu Pro Thr Ala Leu Asp Gly Phe
                85                  90                  95

Ser Leu Glu Ala Met Leu Thr Ile Tyr Gln Leu His Lys Ile Cys His
                100                 105                 110

Ser Arg Ala Phe Gln His Trp Glu Leu Ile Gln Glu Asp Ile Leu Asp
            115                 120                 125

Thr Gly Asn Asp Lys Asn Gly Lys Glu Glu Val Ile Lys Arg Lys Ile
    130                 135                 140

```
Pro Tyr Ile Leu Lys Arg Gln Leu Tyr Glu Asn Lys Pro Arg Pro
145                 150                 155                 160

Tyr Ile Leu Lys Arg Asp Ser Tyr Tyr Tyr
                165                 170

<210> SEQ ID NO 2
<211> LENGTH: 13
<212> TYPE: PRT
<213> ORGANISM: Homo Sapiens

<400> SEQUENCE: 2

Gln Leu Tyr Glu Asn Lys Pro Arg Arg Pro Tyr Ile Leu
1               5                   10

<210> SEQ ID NO 3
<211> LENGTH: 6
<212> TYPE: PRT
<213> ORGANISM: Homo sapiens

<400> SEQUENCE: 3

Lys Ile Pro Tyr Ile Leu
1               5

<210> SEQ ID NO 4
<211> LENGTH: 19
<212> TYPE: PRT
<213> ORGANISM: Artificial
<220> FEATURE:
<223> OTHER INFORMATION: Synthetic pepitde

<400> SEQUENCE: 4

Asn Leu Asn Ser Pro Ala Glu Glu Thr Gly Glu Val His Glu Glu
1               5                   10                  15

Leu Val Ala

<210> SEQ ID NO 5
<211> LENGTH: 20
<212> TYPE: PRT
<213> ORGANISM: Artificial
<220> FEATURE:
<223> OTHER INFORMATION: Synthetic peptide

<400> SEQUENCE: 5

Leu Ile Gln Glu Asp Ile Leu Asp Thr Gly Asn Asp Lys Asn Gly Lys
1               5                   10                  15

Glu Glu Val Ile
            20

<210> SEQ ID NO 6
<211> LENGTH: 117
<212> TYPE: PRT
<213> ORGANISM: Homo sapiens

<400> SEQUENCE: 6

Ser Asp Ser Glu Glu Glu Met Lys Ala Leu Glu Ala Asp Phe Leu Thr
1               5                   10                  15

Asn Met His Thr Ser Lys Ile Ser Lys Ala His Val Pro Ser Trp Lys
                20                  25                  30

Met Thr Leu Leu Asn Val Cys Ser Leu Val Asn Asn Leu Asn Ser Pro
            35                  40                  45

Ala Glu Glu Thr Gly Glu Val His Glu Glu Leu Val Ala Arg Arg
        50                  55                  60
```

-continued

```
Lys Leu Pro Thr Ala Leu Asp Gly Phe Ser Leu Glu Ala Met Leu Thr
65              70                  75                  80

Ile Tyr Gln Leu His Lys Ile Cys His Ser Arg Ala Phe Gln His Trp
                85              90                  95

Glu Leu Ile Gln Glu Asp Ile Leu Asp Thr Gly Asn Asp Lys Asn Gly
            100             105                 110

Lys Glu Glu Val Ile
        115
```

IMMUNOASSAY FOR DETERMINING THE RELEASE OF NEUROTENSIN INTO THE CIRCULATION

CROSS REFERENCE TO RELATED APPLICATIONS

This application is a 371 filing of PCT International application no. PCT/EP2006/000659 filed Jan. 25, 2006 and published in German as WO 2006/079528 on Aug. 3, 2006 which claims the priority of German application no. 10 2005 003 687.2 filed Jan. 26, 2005. The disclosures of these applications and all other patents, published applications and other references cited herein are hereby incorporated by reference in their entirety.

The present invention relates to a method suitable for routine diagnosis and intended for determining the release of the peptide neurotensin into the circulation.

It should first be noted that, for reasons of simplification, terms such as "diagnosis" or "routine diagnosis" are used as a rule in the present description in a global sense which is intended to cover the determination of the measured biomolecules (peptides) not only for diagnostic purposes in the narrower sense but also for other purposes, such as, for example, for the determination of the metabolic state of a test subject before the beginning of a treatment or of an investigation for diagnostic purposes or for observation and monitoring of a patient over relatively long periods, for example for monitoring the course of a disease or therapeutic measures. Determinations for research purposes, for example in combination with the development of pharmaceuticals, for example neurotensin receptor agonists, or of products for nutrition, are also to be subsumed under the term "diagnosis", unless ruled out in specific cases owing to the more specific relationships discussed.

It is also true that applications in the area of veterinary medicine or animal breading are also to be included in principle even when the more specific statements on the invention in the present Application relate in particular to human medicine. Thus, the applicability of most statements on the present invention to non-human mammals is evident to the person skilled in the art without extensive explanations being required. The analogous applicability of the method described in more detail for human medicine to veterinary medicine follows, for example, from the fact that the corresponding peptide sequences are known for many other mammals and, in addition to veterinary applications, applications which relate rather to mammal breeding, for example as monitoring of the feeding state and the feed utilization of commercial animals, are also conceivable.

Neurotensin is a tridecapeptide which occurs in various tissues and in the circulation of various mammals, including humans, and whose primary structure appears to be identical in all mammals. It has the amino acid sequence which is shown in the sequence listing as SEQ ID NO:2.

Like most biologically active peptides (5; references in the form of numbers in brackets relate to the attached list of references), neurotensin is formed by enzymatic processing from a precursor molecule which is referred to as preproneurotensin (with signal sequence) or proneurotensin (PNT; without signal sequence). In addition to the neurotensin (NT), the preproneurotensin/proneurotensin of mammals contains a further biologically active peptide, the hexapeptide neuromedin N (NMN; cf. SEQ ID NO:3). Neurotensin precursor peptides were isolated, inter alia, from canine, bovine and rodent tissues and finally also from human tissues. While the mature peptides NT and NMN have an identical amino acid sequence for different mammals, the precursor molecules, i.e. the preproneurotensins or proneurotensins, of different mammal species differ with regard to a number of amino acids. Thus, rat or bovine preproneurotensin has, for example, only 169 amino acids, whereas human preproneurotensin has 170 amino acids (17).

The nucleotide and amino acid sequences of human preproneurotensin have been known for some years (SEQ ID NO:1; cf. also U.S. Pat. No. 6,274,720 B1), exactly like those of dog (9), rat (17) and cattle (17; cf. also the comparison of different preproneurotensin sequences in FIG. 2 of the above-mentioned US patent). The amino acids 1 to 23 of preproneurotensin (SEQ ID NO:1) represent the so-called signal sequence.

The expression of proneurotensin takes place primarily in the central nervous system (CNS) and in special enteroendocrine cells, the so-called N cells in the distal small intestine, and in nerve fibers which pass through the intestinal tract (13). However, PNT and NT were also detected in the adrenal glands and in heart tissue (24; 23).

The biologically active neurotensin (NT) formed from proneurotensin was detected in various mammalian tissues and discussed in relation to numerous different functions. Thus, neurotensin plays a major role as a neurotransmitter in the brain and has analgesic and thermoregulatory effects (6; 8) Furthermore, NT regulates the release of the neurotransmitters acetylcholine and glutamate (19; 18), stimulates the secretion of pituitary hormones (29) and influences dopamine neurotransmission (18), which suggests a relationship with Parkinson's disease (28).

The secretion of neurotensin in the gastrointestinal tract is stimulated by food intake (15). Even shortly after eating, there is a significant NT increase which persists over several hours (14). It was possible to show that the consumption of fat, in comparison with protein and glucose, had the strongest influence on NT production (27). Neurotensin evidently represents a sort of "saturation factor" since the secretion of NT leads to suppression of the appetite and hence to reduction of food consumption (34). In adipose (obese) patients, the plasma concentration of NT is reduced in comparison with persons of normal weight, which is presumably due to an increased appetite and increased consumption of food (35; 4). Interestingly, smokers, too, showed a significantly greater increase in the NT concentration after food consumption than nonsmokers (26). This indicates that a changed neurotensin secretion is a possible cause of the increased appetite and the frequently observed weight increase of former smokers after stopping smoking.

In the gastrointestinal tract, neurotensin stimulates the secretion of pancreas hormones such as insulin and glucagon, inhibits the secretion of gastric acid and stimulates the motility of the large intestine (33). NT promotes the growth of gastrointestinal tissue, such as pancreas, large intestine and small intestine tissue (12; 36; 10), which gives rise to the hypothesis that NT contributes to the formation of tumors in these tissues.

The function of the second peptide neuromedin N (SEQ ID NO:3), formed from the same precursor peptide, is less well characterized. Presumably, it has effects similar to those of neurotensin since the two have similarities in their amino acid sequence and bind to the same receptors (33).

By investigating different tissue extracts with the use of radioimmunoassays employing antibodies which are specific for free C-termini of NT or NMN and therefore do not recognize proneurotensin forms not proteolytically processed and without such exposed COOH termini, partly in combination with HPLC techniques for separating the fractions according to their molecular size, it was found that, in addition to NT and NMN, incompletely cleaved, so-called large NT and/or NMN peptides can also be formed in the processing of PNT in a tissue-dependent manner (7; 13; 25).

Numerous investigations are concerned with the formation or the occurrence of neurotensin in various diseases, these investigations having been carried out primarily with tissue samples and tissue extracts. Regarding investigations which are based on measurements of neurotensin in patients' blood samples, it should be mentioned, for example, that the concentration of neurotensin in the plasma of patients with Parkinson's disease was found to be increased (30). In celiac patients who have an intolerance to cereal gluten, an increased neurotensin concentration was detected in the plasma in comparison with control persons in the fasted state (2). The plasma concentrations of neurotensin in patients with pancreatitis are increased after a meal in comparison with healthy control persons (22). In the case of thyroid diseases, significantly lower neurotensin concentrations were found in the plasma of patients with central (or secondary) thyroid underfunction (31). Secondary thyroid underfunction is caused by a disturbance in the region of the pituitary gland, which controls the secretion of thyroid hormones. On the other hand, significantly higher neurotensin levels (31) were found in the blood of patients with peripheral (or primary) thyroid underfunction or thyroid overfunction in comparison with controls. Primary thyroid underfunction is caused by dysfunction of the thyroid itself. Patients with cystic fibrosis (mucoviscidosis) have higher neurotensin concentrations in the plasma than healthy control persons both before and after food consumption (16; 1; 21).

The neurotensin levels in blood were invariably determined using assays of the radioimmunoassay type, in which the competition of the neurotensin to be determined in the sample with an added marked neurotensin or neurotensin fragment for the binding sites of a single antibody which binds specifically to neurotensin or certain partial sequences of free neurotensin, for example with a free C-terminus of neurotensin, is determined. Measurements of the NMN levels were carried out in a similar manner.

The above and similar results for the occurrence of neurotensin in the case of certain diseases and the demonstrated possibility of stimulating neurotensin formation as a function of food consumption, which also proved to be significantly different for certain pathological states, make the determination of neurotensin in blood samples an essentially promising and clinically versatile diagnostic tool. Thus, it appears possible to use such a determination, for example, in the routine investigation of patients, for their monitoring during their clinical care, for monitoring of their ability to utilize food, in monitoring of the intestinal functions or as a therapy-accompanying measure for monitoring the success of treatments, as well as in other contexts which arise out of the abovementioned discussion of the scientific literature.

However, neurotensin determinations in blood samples have not to date been adopted in routine medical diagnosis. A first substantial reason for this is that the stability of the neurotensin concentrations in the blood samples ex vivo at ambient temperature is too low for routine measurements (20) (half-life of only 3 to 4 h), which, in combination with existing laboratory logistics (of sampling, plasma recovery, transport to the laboratory up to carrying out of corresponding laboratory tests) has so far prevented the use of neurotensin in routine diagnosis. A second reason is the known short half-life of only 2 to 6 min for neurotensin in blood in vivo, which is attributed to rapid and effective binding to neurotensin receptors and/or degradation of the neurotensin (3) and burdens a measurement with a time dependence which is potentially difficult to estimate. Instantaneously measurable NT levels in blood samples are not a measure of the total biosynthesis and release of NT into the circulation as a result of a stimulation, e.g. supply of food, up to the time of measurement, but rather represent a random transitional state in which the NT elimination by binding to receptors and by degradation greatly dilutes the inflammation on the biosynthesis and release into the circulation.

It is an object of the present invention to provide a possibility for determining the neurotensin release in samples of test mammals, in particular human patients, which is suitable for routine use and makes it possible to utilize the potential outlined above for a determination of the neurotensin release for medical diagnosis and to implement it for medical/clinical routine.

This object is achieved by an immunodiagnostic assay method for determining the release of neurotensin into the mammalian circulation, which method, in its most general form, is characterized in that an immunoreactivity of the N-terminal portion of a mammalian proneurotensin (PNT immunoreactivity) is selectively determined in a serum sample or plasma sample of a test mammal, said immunoreactivity not being a neurotensin or neuromedin N immunoreactivity.

The object is furthermore achieved by a kit for a preferred embodiment of such a method.

Below, the novel discoveries on which the invention is based, and the applications according to the invention which are derived therefrom, are explained in more detail with reference to specific test results and figures.

"Immunoreactivity of the N-terminal portion of mammalian proneurotensin" means an immunoreactivity which is localized in the region of the amino acid in position 24 (position 1 after the signal peptide) up to the third last amino acid before the first amino acid of neuromedin N (Lys) of the respective mammalian preproneurotensin. In all known cases, the region discussed comprises at least the respective amino acids 24 to 139 or 140, i.e. a sequence as shown for the human peptide in SEQ ID NO:6.

To examine the question as to whether reproducible results which correspond to the literature data on the occurrence of NT can be obtained in a determination of an immunoreactivity which is to be assigned to an N-terminal portion of human proneurotensin, in particular a portion which contains neither NMN nor NT and is eliminated in the proteolytic processing with formation of free NMN or NT and then represents a sort of waste product, in a blood sample or serum sample or plasma sample, a sandwich assay specific for this N-terminus of PNT, as described in more detail in the experimental section, was developed. This assay specifically recognizes only N-terminal peptides of human PNT, which contain both the amino acids 67 to 85 and the amino acids 121 to 140 of human preproneurotensin.

Measurements of human blood samples using this assay, which are described below in more detail, showed that PNT immunoreactivities which, according to occurrence and dynamics, reflect the formation/release of NT are measured therewith.

In the case of the repeated measurement of serum samples and plasma samples obtained from such blood samples on storage at room temperature over relatively long periods, it was furthermore found that the stability of the PNT immunoreactivity in plasma ex vivo is surprisingly high. Since no recognizable loss of determinable immunoreactivity was detectable even after 7 days, its half-life at room temperature is far more than 7 days and hence well above the ex vivo stability of mature neurotensin (cf. 3) or that of one of the large, incompletely processed proneurotensin peptides.

Figure 1:
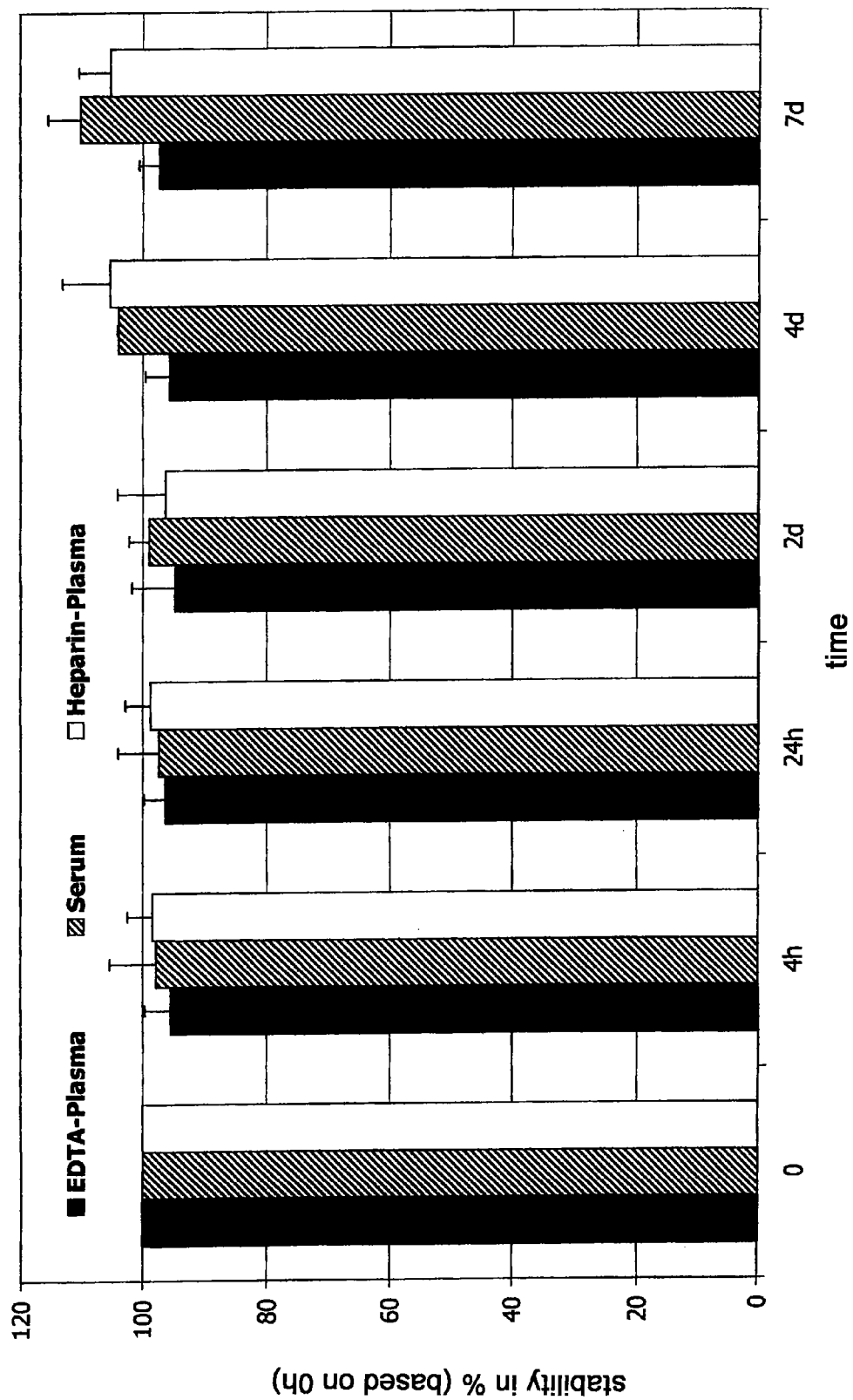
FIG. 1 shows results of the measurement of the ex vivo stability of the immunoreactivity which is to be assigned to N-terminal sequences of human PNT, in serum, EDTA plasma and heparin plasma samples obtained from the blood of test subjects, at room temperature over periods of up to 7 days.

The results of the stability measurements are shown in FIG. 1.

Thus, the determination of proneurotensin or PNT fragments in blood samples is entirely fit for routine use and is suitable for making the NT/NMN/PNT release rate in the blood accessible to routine medical diagnosis.

The preparation of the assay used, its use in measurements and the measured results obtained with it are described more exactly in the following experimental section and the examples and the associated explanations.

EXPERIMENTAL SECTION

Determination of an immunoreactivity to be assigned to N-terminal proneurotensin sequences.
1. Preparation of Antibodies
1.1. Immunogens 2 different peptide partial sequences of human preproneurotensin (SEQ ID NO:1), namely PNT3 (SEQ ID NO:4) and PNT4 (SEQ ID NO:5), were selected and were synthesized as synthetic peptides by Jerini (Berlin, Germany). Each peptide was additionally provided with an amino-terminal cysteine residue (Cys0).
1.2. Antibody Recovery For immunization purposes, the peptides PNT3 (SEQ ID NO:4) and PNT4 (SEQ ID NO:5) supplemented by N-terminal cysteine residues were conjugated with the hemocyanine from *Limulus polyphemus* and used according to standard methods for immunizing rabbits, from which antisera against the PNT peptide conjugates were obtained.
1.3. Purification of the Antibodies The polyclonal antibodies of the rabbit antisera were purified by means of ligand-specific affinity purification. For this purpose, the Cys(0) peptides PNT3 (SEQ ID NO:4) and PNT4 (SEQ ID NO:5) were first coupled to SulfoLink gel from Pierce (Boston, USA). The binding was effected by the manufacturer's method as follows:

Polycarbonate columns (15 mm×80 mm) were filled with 5 ml of affinity matrix. After equilibration of the columns with PBS (136 mM NaCl, 1.5 mM $KH_2PO_4$ 20.4 mM $Na_2HPO_4.2H_2O$, 2.7 mM KCl, pH 7.12), 5 mg of the respective abovementioned peptides were weighed out, dissolved in PBS and added to the closed columns, and the gel material was homogenized by swirling. After incubation for 15 minutes at room temperature and settling of the gel material, the columns were washed 5 times with 3 ml portions of PBS. For saturation of free binding sites 5 ml of 50 mM L-cysteine solution were added in each case to the column material and, after homogenization, the gel material was incubated again at room temperature for 15 min. After settling of the gel material, each column was rinsed 6 times with 5 ml portions of a 1 M NaCl solution and then rinsed again with PBS.

The gel material was mixed with 25 ml of the respective rabbit antiserum pool and incubated over night at room temperature with gentle swirling. The serum-gel mixtures were transferred to polycarbonate columns and excess serum was removed. The columns were then washed with 250 ml of PBS in order to remove serum proteins which were not bound. The desorption of the bound antibodies was effected by elution of the column with 50 mM citric acid (pH 2.2). The eluate was collected in 1 ml fractions. The protein concentration of each fraction was determined with the aid of the BCA protein assay kit from Perbio (Bonn, Germany), and fractions having a protein content of >1 mg/ml were combined. The affinity-purified antibodies were rebuffered by means of dialysis in PBS and the protein content was determined again. Storage was then carried out at 4° C.
2. Assay Preparation
2.1. Solid Phase The affinity-purified polyclonal rabbit antibody against the peptide PNT3 was immobilized on polystyrene tubes (Startubes, 12 mm×75 mm, from Greiner, Germany). For this purpose, the antibody solution was diluted to a protein concentration of 6.7 µg/ml with PBS, and 300 µl thereof were pipetted per tube (corresponds to 2 µg of antibodies per tube). These were incubated for 24 h at room temperature and then washed 3 times with 4 ml portions of PBS. The tubes were stored at 4° C. until required for further use.
2.2. Marked Antibodies The affinity-purified polyclonal rabbit antibody against PNT4 (1 mg/ml in PBS) was luminescence-marked with acridinium ester N-hydroxysuccinimide (1 mg/ml in acetonitrile, from InVent, Hennigsdorf, Germany). For the marking, 200 µl of antibodies were mixed with 4 µl of acridinium ester and incubated for 20 min and free acridinium ester bonds were saturated by addition of 40 µl of a 50 mM glycine solution. The marking batch was separated from free acridinium ester by means of HPLC on a BioSil 400 gel filtration column (from BioRad, Munich, Germany). The mobile phase used was PBS.
3. Carrying Out PNT Determinations
3.1.1 Measuring Conditions 50 µl of a plasma sample to be investigated and 150 µl of assay buffer (PBS buffer, 10 mM EDTA) were pipetted antibody-coated tube (2.1) and incubated for 16 h at room temperature. The tubes were then washed 5 times with 1 ml portions of PBS. 20 ng of the marked antibody (2.1.) (in 100 µl of PBS buffer, 10 mM EDTA) were then added to each of the tubes. The tubes were incubated for 2 h at room temperature, and unbound tracer antibody was then removed by washing 5 times with 1 ml portions of PBS.

Figure 2:
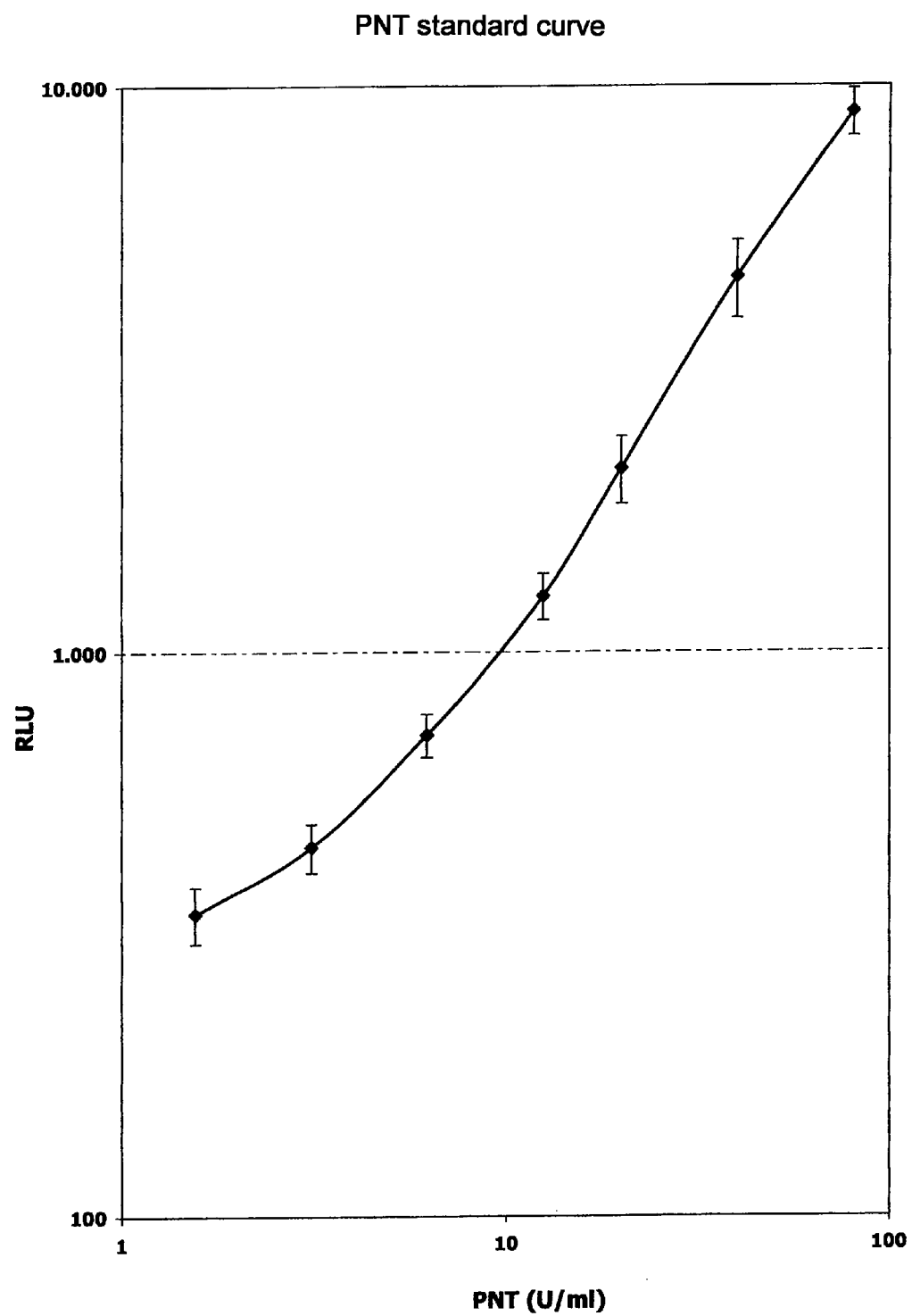
FIG. 2 shows the standard curve of a PNT sandwich assay as described in more detail in the experimental section.

Marked antibody bound to the tube was quantified by means of luminescence measurement in a commercial luminometer (Berthold LB 952T/16).
3.2. Calibration In order to be able to determine the concentrations or immunoreactivities of proneurotensin in the samples to be measured, 50 EDTA plasmas of apparently healthy persons were screened for PNT, and plasmas having the highest PNT immunoreactivities were pooled. From this plasma pool, a plurality of dilution stages were produced with horse serum (Sigma, Germany). A fictitious concentration of 100 units/ml was assigned to the highest standard (undiluted EDTA plasma). FIG. 2 shows a PNT standard curve. The analytical sensitivity of the proneurotensin assay is about 1 U/ml.

Figure 4:
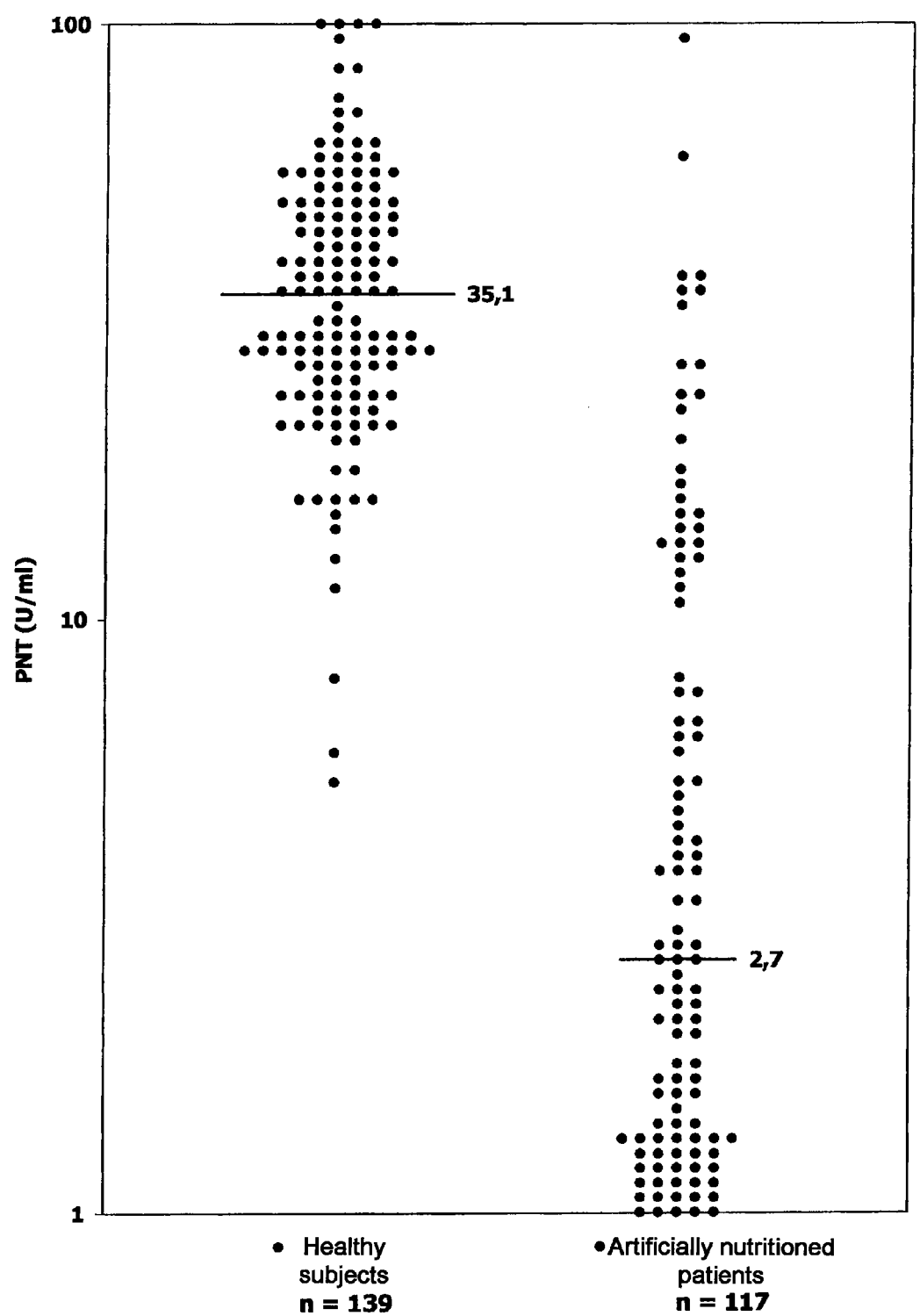
FIG. 4 shows the results of the measurement of changes of the PNT immunoreactivity as a function of time in the plasma of normally fed normal persons, depending on the supply of food, by means of the sandwich assay described.

4. Results of Measurements 4.1. Proneurotensin Immunoreactivity in Plasmas of Apparently Healthy Persons Apparently healthy control persons have high measured PNT values in the blood. There is a frequency distribution, which is shown in FIG. 4. The median was determined as 35.1 U/ml.

4.2. Determination of the PNT Immunoreactivity in the Circulation of Healthy Test Subjects During and after the Consumption of Food It is known that the formation or release of neurotensin is stimulated by consumption of food (15; 14). In order to determine whether the PNT concentration in the blood is also influenced by the consumption of food and whether the dynamics of any change in the PNT immunoreactivity runs parallel to the above-described concentration of NT, the following test was carried out: 6 test subjects (three male and three female persons) fasted for 14 h. A blood sample was then taken from them. The test subjects then consumed a defined amount of liquid or food at specified times, and blood samples were taken again at certain times. The course of the test is summarized in table 1.

TABLE 1

Course of the food stimulation test

| Sampling point | Nutrition status |
|---|---|
| 1 | after fasting for 14 h |
| 2 | after fasting for 15 h |
| 3 | 5 min after liquid intake (1 l of water) |
| 4 | 15 min after liquid intake |
| 5 | 45 min after liquid intake |
| 6 | 1 h 15 min after liquid intake |
| 7 | 1 h 45 min after liquid intake |
| 8 | 3 h after liquid intake |
| 9 | 5 min after consumption of food (salad with approx. 250 kcal and pizza with approx. 100 kcal) |
| 10 | 15 min after consumption of food |
| 11 | 30 min after consumption of food |
| 12 | 1 h after consumption of food |
| 13 | 2 h after consumption of food |
| 14 | 3 h after consumption of food |
| 15 | 4 h after consumption of food |

Figure 3:
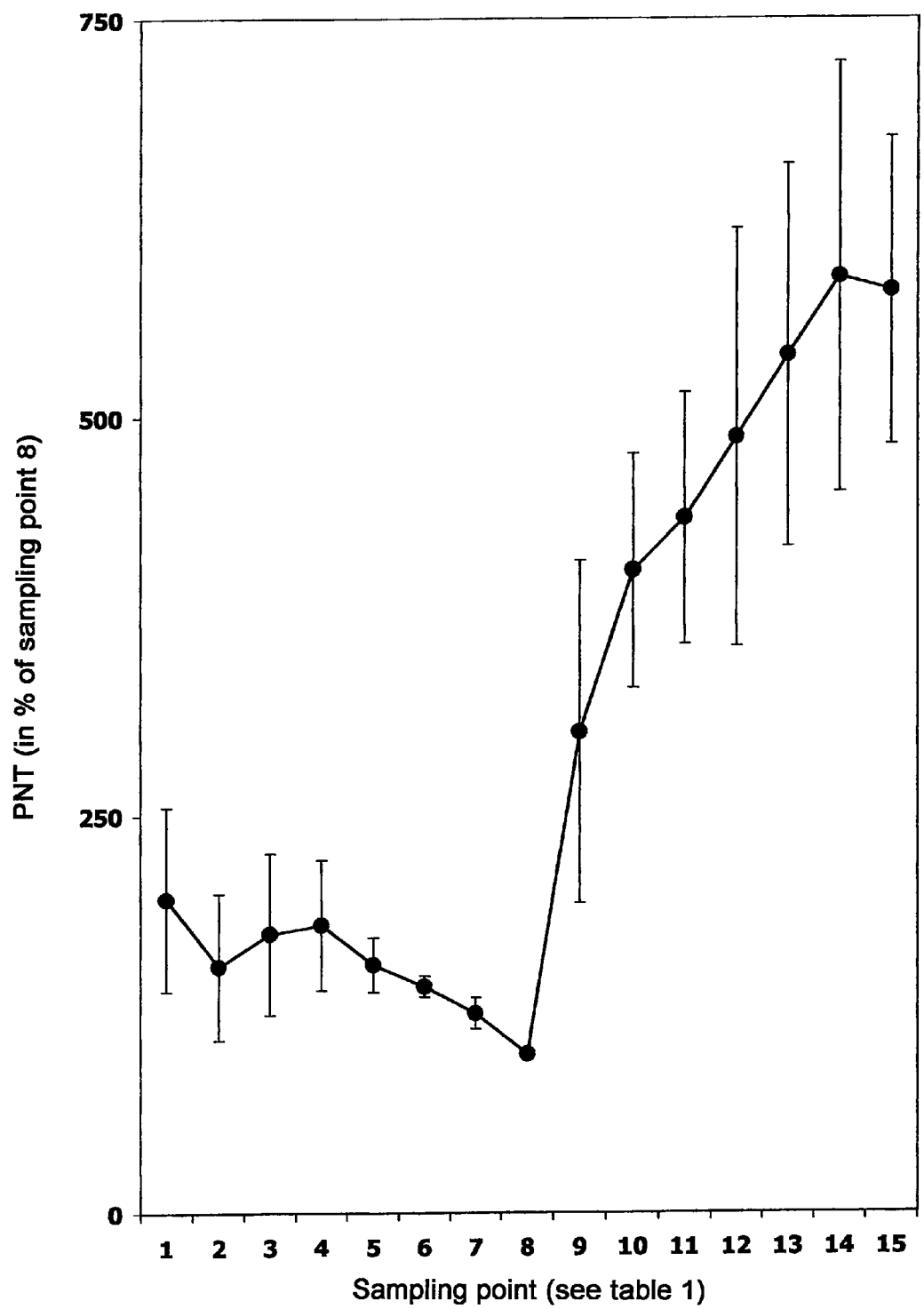
FIG. 3 shows the results of the measurement of the PNT immunoreactivity in plasma in the case of normally fed normal persons and artificially fed patients by means of the sandwich assay described.

It is found that the secretion of PNT is not stimulated by intake of liquid. Shortly before the consumption of food, i.e. after the longest fasting time, the PNT concentration is the lowest. It was defined as 100% for each individual test subject, and all other measurements of the respective test subject were based on this value. These percentage changes of the measured PNT immunoreactivity of the 6 test subjects were averaged and are shown graphically in FIG. 3 ($P<0.05$). Immediately after eating, the PNT concentration in the blood increases significantly. The last two sampling times 3 h and 4 h after consumption of food have the highest measured values. Overall, the PNT concentration increases by 4.5 to 8 times after eating.

Immunoreactivity which can be determined by the above-mentioned assay and is to be coordinated with one or more N-terminal proneurotensin fragment(s) having binding sites for the two antibodies used thus increases, as described for the mature peptide NT, owing to stimulation by consumption of food.

The measurement of PNT immunoreactivity can therefore be used instead of the mature neurotensin for evaluating the metabolic status of a patient/test person. By administration of a defined amount of nutrients, the individual stimulability of the PNT release can be determined as the difference $\Delta$ between a measured value at a specified time after the consumption of food and a base value (e.g. $PNT_{3h\ after\ consumption\ of\ food}$ and $PNT_{fasted}$) or as a ratio or factor of such values. Table 2 shows a corresponding evaluation by way of example.

TABLE 2

PNT immunoreactivities (in U/ml) before and after food simulation and indication of absolute differences and factors

| | Test subject 1 | Test subject 2 | Test subject 3 | Test subject 4 | Test subject 5 | Test subject 6 |
|---|---|---|---|---|---|---|
| $PNT_B$ | 10.5 | 2.3 | 4.8 | 5.0 | 5.7 | 5.8 |
| $PNT_{5\ min}$ | 32.3 | 10.7 | 9.6 | 23.0 | 27.1 | 15.5 |
| $PNT_{3\ h}$ | 42.4 | 18.4 | 20.0 | 22.7 | 41.5 | 40.6 |
| $\Delta$ $PNT_{5\ min}$ minus $PNT_B$ | 21.8 | 8.45 | 4.8 | 18.0 | 21.4 | 9.7 |
| $\Delta$ $PNT_{3\ h}$ minus $PNT_B$ | 31.9 | 16.1 | 15.2 | 17.7 | 35.8 | 34.8 |
| $PNT_{5\ min}/PNT_B$ | 3.1 | 4.7 | 2 | 4.6 | 4.8 | 2.7 |
| $PNT_{3\ h}/PNT_B$ | 4.0 | 8 | 4.2 | 4.5 | 7.3 | 7 |

In the table, the meanings are as follows:
$PNT_B$ = PNT immunoreactivity after fasting for 18 h (base value)
$PNT_{5\ min}$ = PNT immunoreactivity 5 min after consumption of food
$PNT_{3\ h}$ = PNT immunoreactivity 3 h after consumption of food 4.3. Determination of the PNT Concentrations in the Circulation of Artificially Fed Patients As already shown, healthy persons have a certain blood PNT concentration which can be stimulated by consumption of food. In a corresponding measurement of the PNT immunoreactivity in plasmas of patients artificially fed parenterally (by means of a vein catheter) and generally in intensive care (for example with an existing sepsis or a polytrauma), it was found that they have significantly lower PNT concentrations than normally fed controls. In such measurements, a median relative PNT immunoreactivity of 2.7 U/ml, a factor of 13 lower, was found (cf. FIG. 4).

4.4. Determination of the PNT Immunoreactivity in the Circulation of Patients with Inflammatory Intestinal Diseases (Crohn's Disease or Colitis Ulcerosa)

In the measurement of samples of patients with an inflammatory intestinal disease, such as Crohn's disease and Colitis ulcerosa, it was found that here too the median measurable PNT immunoreactivity of 10 U/ml is below that of the control persons (FIG. 5) However, individuals among the patients also had substantially higher measured values (above 100 U/ml).

Figure 5:
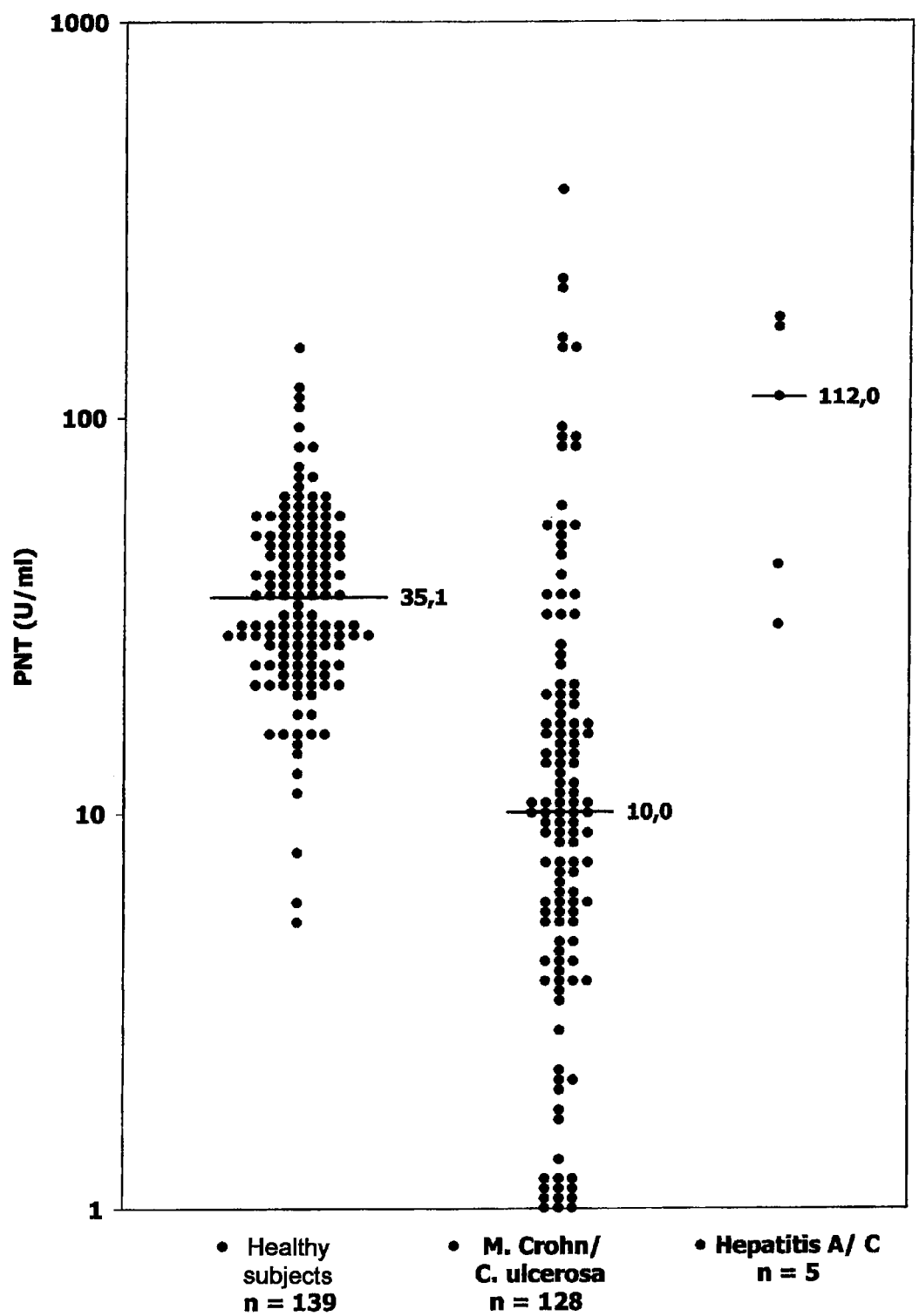
FIG. 5 shows the results of the measurement of the PNT immunoreactivity in plasma in the case of normally fed normal persons, patients with chronic inflammatory intestinal diseases (Crohn's disease/Colitis ulcerosa) and hepatitis patients by means of the sandwich assay described.

4.5. Determination of the PNT Immunoreactivity in the Circulation of Patients Having a Hepatitis a or C In the measurement of samples of patients with a hepatitis A or C, on the other hand, higher PNT concentrations were found in the circulation, with a median of 112 U/ml, compared with the healthy controls (FIG. 5).

5. Isolation and Characterization of Proneurotensin Immunoreactivity in Human Serum 5.1. Preparation of the Affinity Column 5 mg of the purified polyclonal rabbit antibody against the PNT3 peptide (SEQ ID NO:4; cf. 1.1.) were coupled to 2 ml of CarboLink gel (from Pierce, Boston, USA), according to the manufacturer's method and transferred to a polycarbonate column (15 mm×80 mm). The gel was then washed with 20 ml of PBS.

5.2. Affinity Purification of PNT Immunoreactivity

A mixed serum sample comprising 10 individual sera of 100 ml with a relative concentration of 32 U/ml was mixed with Na EDTA (final concentration 10 mM) and then filtered over 0.2 μm filter. The prepared mixed serum sample was pumped at 4° C. and at a flow rate of 2 ml/min six times in succession over the affinity column. Thereafter, the column was washed with 50 ml of PBS and the bound PMT immunoreactivity was eluted with a 50 mM glycine/HCl solution (pH 2.0). The column outflow was monitored continuously for absorption at 280 nm and the protein fraction (final volume 3 ml) eluted by the glycine/HCl solution was further analyzed by means of HPLC.

5.3. Reversed-Phase HPLC Analysis

The material obtained by affinity purification was purified by means of reversed-phase HPLC on a $C_{18}$ column μBondapak 0.4×30 mm from Waters (Eschborn, Germany). The flow rate of 1 ml/min. The mobile phase and elution conditions used are shown in table 3 below.

TABLE 3

Elution conditions of the RP-HPLC of proneurotensin-IR

Mobile phase A:
5% acetonitrile
20 mM $NH_4$ acetate
Mobile phase B:
90% acetonitrile
20 mM $NH_4$ acetate TABLE 3-continued Elution conditions of the RP-HPLC of proneurotensin-IR

| Gradient | 0.0 min | 100% A/0% B |
|---|---|---|
| | 2.5 min | 100% A/0% B |
| | 5.0 min | 89% A/11% B |
| | 55.0 min | 30% A/70% B |
| | 60.0 min | 0% A/100% B |

The column outflow was measured continuously for its absorption at 215 nm and collected in 0.5 ml fractions. With the aid of the PNT assay described in the above sections 2. and 3., those fractions in which a PNT immunoreactivity was detectable were determined. It was found that the main immunoreactivity was eluted in fraction 67.

Fraction 67, which had a positive PNT immunoreactivity, was dried by treatment with nitrogen gas. Samples were then analyzed by mass spectrometry.

5.4. Mass Spectrometric Analysis

The peptide was digested by means of protease Glu-C or trypsin and the resulting fragments were obtained in a manner known per se via SMART HPLC and then investigated by mass spectrometry.

In the mass spectrometric analysis, a sequence (SEQ ID NO:6) which agreed completely with the sequence of the amino acids 24-140 of the known preproneurotensin 1-170 (SEQ ID NO:1) was determined. It was thus shown that a proneurotensin peptide which comprises 117 amino acids and is designated as preproneurotensin 24-140 circulates in the blood of humans. There was no indication at all that the species determined as immunoreactivity by means of the method described still contains the C-terminal mature peptides neuromedin N and neurotensin.

The invention claimed is:

1. An immunoassay method for determining the release of neurotensin, a polypeptide consisting of amino acids 151-163 of preproneurotensin, a polypeptide of SEQ ID NO:1, into the circulation of a mammal, the method comprising:
   a) contacting a plasma or serum sample obtained from said mammal with a first and a second antibody, wherein
      i. said first and second antibodies, respectively, specifically bind to one or more amino acids of two different regions within amino acids 24-140 of SEQ ID NO:1, a partial peptide of preproneurotensin, and
      ii. at least one of the first and second antibodies comprises a detectable label; and
   b) detecting the amount of label bound to the peptide within amino acids 24-140 of SEQ ID NO:1, a partial peptide of preproneurotensin, in said sample,
wherein the amount of label indicates the amount of neurotensin released into the circulation of said mammal.

2. An immunoassay method for determining the amount of neurotensin, a polypeptide consisting of amino acids 151-163 of preproneurotensin, a polypeptide of SEQ ID NO:1, released into the circulation of a mammal, the method comprising:
   a) contacting a plasma or serum sample obtained from said mammal with
      i) a first antibody that specifically binds to one or more amino acids of a first peptide within amino acids 67 to 85 of SEQ ID NO:1, of the N-terminal portion (amino acids 24-140 of SEQ ID NO:1) of proneurotensin (amino acids 24-170 of SEQ ID NO:1), wherein said antibody does not bind to neurotensin (amino acids 151-163 of SEQ ID NO:1) or neuromedin N (amino acids 143-148 of SEQ ID NO:1), and
      ii) a second antibody that specifically binds to one or more amino acids of a second peptide within amino acids 121 to 140 of SEQ ID NO:1,
wherein at least one of said first and second antibodies is labeled with a detectable marker, and
   b) measuring the amount of detectable marker and thereby detecting of the N-terminal portion of mammalian proneurotenisn in said sample,
wherein the amount of detectable marker indicates the amount of neurotensin released into the circulation of the mammal.

3. The method of claim 1, wherein said first and second antibodies are both monoclonal, both affinity-purified polyclonal antibodies or a combination of monoclonal and affinity-purified polyclonal antibodies.

4. The method of claim 1, wherein said first antibodies are obtained by immunization of an animal with a synthetic peptide consisting of amino acids 67 to 85 (SEQ ID NO:4) of human preproneurotensin (SEQ ID NO:1), and said second antibodies are obtained by immunization with a synthetic peptide consisting of amino acids 121 to 140 (SEQ ID NO:5) of human preproneurotensin (SEQ ID NO:1).

5. The method of claim 1, wherein one of said first and second antibodies is bound to a solid phase, and the other antibody comprises a detectable label.

6. The method of claim 1, wherein said detectable label is selected from the group consisting of a radioisotope chemiluminescent, bioluminescent, fluorescent and enzyme label.

7. The method of claim 1, wherein both first and second antibodies are used in dispersion in a liquid reaction mixture and both first and second antibodies comprise detectable labels that are part of a marker system based on fluorescence or chemiluminescence extinction or amplification wherein, after binding of both first and second antibodies to the proneurotensin partial peptide to form proneurotensin partial peptide/antibody complexes, a measurable signal is produced which permits detection of proneurotensin partial peptide/antibody complexes in the liquid reaction mixture.

8. The method of claim 7, wherein the marker system comprises rare earth cryptates or chelates in combination with a fluorescent or chemiluminescent dye.

9. The method of claim 1, which is carried out as a point-of-care method with the use of an immunochromatographic measuring apparatus, and a directly visually detectable label is used as a label for marking.

10. The method of claim 1, which is carried out for monitoring the nutrition status and/or the digestive functions of a human patient.

11. The method of claim 10, wherein the patient is artificially fed.

12. A kit for carrying out a method for determining the release of neurotensin which is a polypeptide consisting of amino acids 151-163 of a preproneurotensin polypeptide consisting of SEQ ID NO:1, into a mammalian circulation, said kit comprising:
   a) a first antibody that specifically binds to a first region within amino acids 24-140 of SEQ ID NO:1; and
   b) a second antibody that specifically binds to a second region within amino acids 24 to 140 of SEQ ID NO:1,
   wherein both of said first and second antibodies do not bind to neurotensin (a polypeptide consisting of amino acids 151-163 of SEQ ID NO:1) or neuromedin (a polypeptide consisting of amino acids 143-148 of SEQ ID NO:1), and wherein one of said first and second antibodies is labeled with a detectable marker.

13. The kit of claim 12, wherein said first antibody is generated by immunization with a peptide consisting of the amino acid sequence of SEQ ID NO:4 and the second antibody is generated by immunization with a peptide consisting of the amino acid sequence of SEQ ID NO:5.

* * * * *

UNITED STATES PATENT AND TRADEMARK OFFICE
CERTIFICATE OF CORRECTION

PATENT NO.       : 8,637,256 B2                                           Page 1 of 1
APPLICATION NO. : 11/814850
DATED            : January 28, 2014
INVENTOR(S)      : Andrea Ernst It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 943 days.

Signed and Sealed this
Twenty-second Day of September, 2015

Michelle K. Lee
*Director of the United States Patent and Trademark Office*